United States Patent
Moriarty et al.

(10) Patent No.: US 6,280,635 B1
(45) Date of Patent: Aug. 28, 2001

(54) AUTOCYCLE CONTROL OF COOLING WATER SYSTEMS

(75) Inventors: Barbara E. Moriarty, Palatine; Dennis P. Bakalik, Woodridge; Ronald V. Davis, Geneva; John E. Hoots, St. Charles; Robert W. Shiely, Batavia, all of IL (US)

(73) Assignee: Nalco Chemical Company, Naperville, IL (US)

( * ) Notice: Subject to any disclaimer, the term of this patent is extended or adjusted under 35 U.S.C. 154(b) by 0 days.

(21) Appl. No.: 09/562,603

(22) Filed: May 1, 2000

(51) Int. Cl.$^7$ .................... C02F 1/00; B03D 3/06
(52) U.S. Cl. ............ 210/745; 137/3; 73/861.07; 210/690
(58) Field of Search .............. 73/861.07; 137/3; 436/56; 210/745, 696

(56) References Cited

U.S. PATENT DOCUMENTS

| | | | |
|---|---|---|---|
| 4,783,314 | 11/1988 | Hoots et al. | 422/3 |
| 4,813,973 | 3/1989 | Winnik et al. | 8/647 |

(List continued on next page.)

FOREIGN PATENT DOCUMENTS 1141147  1/1969 (GB).

OTHER PUBLICATIONS

"Water Treatment Dosage Control And Relationship To Performance", J. E. Hoots, Paper No. 260, Corrosion 95, NACE Int'l Annual Conference and Corrosion Show, pp. 260/1–260/11.

(List continued on next page.)

*Primary Examiner*—William Wayner

(74) *Attorney, Agent, or Firm*—Margaret M. Brumm; Thomas M. Breininger

(57) ABSTRACT

An autocycle method to control a cooling water system comprising the steps of:
a) adding a treatment product to said cooling water system, with said treatment product comprising inert tracer and tagged treatment polymer in a set proportion;
b) providing a sufficient number of fluorometers,
c) using said sufficient number of fluorometers to measure the fluorescent signal of said inert tracer and the fluorescent signal of said tagged treatment polymer in the water from the cooling water system;
d) using these measured fluorescent signals from step c) to determine the amount of said tagged treatment polymer present in said cooling water system;
e) comparing the amount of said tagged treatment polymer present to the amount of tagged treatment polymer being fed into the system to determine the consumption of said tagged treatment polymer; and
f) using said consumption of said tagged treatment polymer to control the concentration cycles of said cooling water system, with the proviso that said control is implemented by linking any or all of the following parameters
  i) the flowrate of the make-up water to the cooling water system;
  ii) the flowrate of the treatment product comprising inert tracer and tagged treatment polymer,
  iii) frequency and amount of blowdown flowrate from the cooling water system;
  iv) overall water flowrate through the cooling tower;
  v) overall volume of water in the cooling tower; and
  vi) composition of makeup water;
to the consumption of said tagged treatment polymer, with the provisos that:
  α) the minimum flowrate of treatment product comprising inert tracer and tagged treatment polymer must be sufficient to supply the cooling water system with the requisite amount of tagged treatment product; and
  β) when control is implemented by linking flowrates, the flowrates are balanced.

1 Claim, 3 Drawing Sheets

Control of Pilot Cooling Tower using Consumption Control During Make-up Water Upset

U.S. PATENT DOCUMENTS

| | | | |
|---|---|---|---|
| 4,999,456 | 3/1991 | Fong | 525/351 |
| 5,043,406 | 8/1991 | Fong | 526/304 |
| 5,128,419 | 7/1992 | Fong et al. | 525/351 |
| 5,171,450 | 12/1992 | Hoots | 210/701 |
| 5,408,022 | 4/1995 | Imazato et al. | 526/259 |
| 5,435,969 | 7/1995 | Hoots et al. | 422/14 |
| 5,720,884 | 2/1998 | Wallace et al. | 210/696 |
| 5,817,927 | 10/1998 | Chen et al. | 73/40.7 |
| 5,855,791 | 1/1999 | Hays et al. | 210/696 |
| 6,068,012 | 5/2000 | Beardwood et al. | 137/3 |
| 6,153,110 * | 11/2000 | Richardson et al. | 710/739 |

OTHER PUBLICATIONS

"High Cycle Cooling Tower Operation: Hurdles And Solutions", J.E. Hoots, et al., IWC–99–48, pp. 388–397.

"The Use of Coumarin Derivaties In The Preparation Of Fluorescence–Labeled Poly[N–2–(Hydroxypropyl)methacrylamide]", Jiri Krejcoves, et al., Collection Czechoslov. Chem. Commun. [vol. 45] [1980], pp. 727–731.

"Expert System For Water Treatment", FYI, Chemical Engineering Progress.

"Application Of Expert Systems For Cooling Water Monitoring", Paul A. Burda, et al, Corrosion 95, NACE Int'l Annual Conf. And Corrosion Show, Paper No. 255, pp. 255/1–255/20.

"A New On–Line Monitoring And Control Capability For Cooling Water Programs", J. Richardson, et al., Cooling Tower Institute 1993 Annual Meeting, Technical Paper No. TP93–10, pp. 1–18.

"Approaches for Reducing Phosphorous In Cooling Water Programs", D. Hartwick, et al., Corrosion 96, Paper No. 605, pp. 605/1–605/21.

* cited by examiner

Schematic of Cooling Water System Control Using Fluorescent Tagged Polymer Consumption Control of Pilot Cooling Tower using Consumption Control During Make-up Water Upset

AUTOCYCLE CONTROL OF COOLING WATER SYSTEMS

FIELD OF THE INVENTION

The present invention relates to a method for controlling cooling water systems by measuring the consumption of fluorescent polymers.

BACKGROUND OF THE INVENTION

A cooling water system comprises a cooling tower, heat exchangers, pumps and all necessary piping to move water through the system. Control of a cooling water system is based on balancing the desire to run the cooling water system at the highest concentration cycles possible without incurring detrimental scaling, corrosion, fouling or microbiological control situations.

A concentration cycle is defined for a specific species as:

$$\frac{\text{Specific Species Level in Cooling Water Tower}}{\text{Specific Species Level in Make-Up Water}}$$

For example, when the specific species is the calcium ion (hereinafter "$Ca^{+2}$" or "$Ca^{+3}$" depending on what context it is used in),: if a cooling water system is running at 500 ppm $Ca^{+2}$ with 150 ppm $Ca^{+2}$ in the makeup water, the cooling water system is running at 3.3 concentration cycles. In operating a cooling water system it is desirable to achieve the maximum number of concentration cycles to avoid unnecessary loss of water in blowdown as well as unnecessary overfeeding of treatment chemicals including but not limited to, treatment polymers. The maximum concentration cycles for a cooling water system are limited by the undesirable events, such as scaling and corrosion, which occur when the amount of specific species in the cooling water tower reaches a certain level, such that the species contributes to these problems.

There are several currently known ways used to control the concentration cycles in cooling water systems. Controlling the concentration cycles is typically done by controlling the flow rate of "fresh" water (from one or more sources) known as make-up water into the system and by controlling the main flow rate out of the system, referred to as blowdown. In order to control makeup water flow, a pump or valve controls the flow of make-up water into the cooling tower and a level controller is typically used in the cooling tower reservoir or "sump". The level controller is linked to the make-up water pump or valve and when the water in the sump decreases to a point lower than the setpoint for the level controller the make-up water pump or valve is activated.

Conductivity is the typical method of blowdown control. For purposes of this patent application, conductivity is defined as the measurement of electrical conductivity of water with electrical conductivity being present in the water due to ionic species being present in the water. Conductivity can be used to control bleed of blowdown because conductivity can readily be used to estimate the overall amount of ionic species present in the water and a simple controller can be set to open a valve or pump and start blowdown when the conductivity of the reservoir water reaches above a certain setpoint. There are limits to how useful conductivity is for control of a cooling water system as conductivity is nothing more than an indirect measure of the amount of ionic species present. Therefore, conductivity cannot provide information about scaling tendency or actual scaling and use of conductivity can cause "catastrophic failure", where scaling causes the cooling water system to overcycle and scale further.

Alternatively, a timer can control bleed of blowdown without actually measuring any of the specific species in the water. In addition to or in place of the above control schemes, water flow meters on the make-up and blowdown can be used, in conjunction with a microprocessor controller to do an overall cooling water mass balance.

A problem with these known control schemes, is that when the blowdown is controlled by conductivity and the make-up is controlled by a level controller, if the composition of the usual make-up water is variable, or if there are alternate sources of make-up water that are significantly different from the usual make-up water source, level controllers and conductivity cannot account for all events that are occurring in the system. In these cases, the cooling water system is typically controlled by the operator being conservative with the conductivity setpoint which thus causes extra undesirable expense due to non-optimal use of treatment chemicals and water.

Many cooling water systems use treatment products to control undesirable events such as scaling, corrosion, fouling and microbiological growth. These treatment products comprise polymers and other materials and are known to people of ordinary skill in the art of cooling water systems. A cooling water control system can be set up to feed treatment product based on either a bleed/feed mechanism where the action of blowdown triggers a chemical feed pump or valve that feeds treatment product; or, in the alternative, the cooling water control system feeds treatment product based on timers using a "feeding schedule" or flow meters on the make-up water line trigger the pumping of treatment product based on a certain amount of make-up water being pumped. A limitation of these control methods is that none of these systems measure the treatment product concentration directly online, so if there is a mechanical problem, for example, if a pump fails, a drum empties, or high, low or unknown blowdown occurs, system volume changes or makeup water quality changes; the correct treatment product concentration is not maintained. Because this problem is common, typically cooling water systems are either overfed to ensure the level of treatment product in the system does not drop too low as a result of high variability in product dosage or the treatment product is unknowingly underfed. Both overfeeding and underfeeding of treatment product are undesirable due to cost and performance drawbacks.

One aspect of known control schemes is an inert fluorescent chemical being added to the cooling water system in a known proportion to the active component of the treatment product feed and the use of a fluorometer to monitor the fluorescent signal of the inert fluorescent chemical. This is commercially available as TRASAR®. TRASAR® is a registered trademark of Nalco Chemical Company One Nalco Center, Naperville, Ill. 60563 (630) 305–1000). The fluorescent signal of the inert fluorescent chemical is then used to determine whether the desired amount of treatment product is present in the cooling tower (and to control blowdown).

Many current cooling towers use inert fluorescent tracers to control the treatment product level in the system and also use a conductivity controller to measure the conductivity in the water.

Cooling towers that use both inert tracer(s) and conductivity typically use the following types of information in order to control the tower. For example, a cooling tower with typical makeup water having: 150 ppm $Ca^{+2}$, 75 ppm $Mg^{+2}$, and 100 ppm "M alkalinity"; with a conductivity of 600 $\mu$S/cm (note that conductivity is expressed in units of microsiemans per centimeter), is set to run at 500 ppm $Ca^{+2}$. In order to operate within acceptable levels, the cycles of concentration for this cooling water system are 3.3 (calculated by dividing 500 by 150). Running the system at 500 ppm $Ca^{+2}$ corresponds to a conductivity setpoint of 3.3 times 600 or 1980 $\mu$S/cm. When the conductivity exceeds this setpoint the system is configured to automatically blow-down a portion of "concentrated" cooling water ("concentrated" referring to system water with an unacceptably high level of ions) which is replaced with "fresh" makeup water (where "fresh" is defined as having a lower level of scaling ions than the "concentrated" cooling water). This decreases the conductivity and hardness ($Ca^{+2}$ and $Mg^{+2}$) ions via dilution. Dilution also reduces the amount of inert tracer chemical in the system. Decreasing the amount of inert tracer in the system decreases the fluorescent signal from the inert tracer. When the fluorescent signal from tracer decreases, the tracer control system is set up to feed a fresh mixture of treatment product and inert tracer chemical to makeup for the decrease in fluorescence that was lost in the blowdown.

A known method of control of product feed to a cooling water system involves the use of another aspect of tracer technology. This involves using a treatment product containing a polymer that has been "tagged" with a fluorescent moiety. These tagged treatment polymers are not inert, rather, they are supposed to be consumed as they function to treat whatever performance-related condition it is that they are designed to treat. Thus, by measuring the fluorescent signal of the tagged treatment polymer it is possible to determine the amount of consumption of the tagged treatment polymer. By knowing the amount of consumption of the tagged treatment polymer it is possible to use that information to control the feeding of new treatment product containing tagged treatment polymer.

A recent reference in this area is entitled "High Cycle Cooling Tower Operation: Hurdles and Solutions", Hoots et al, pp. 388–397, was presented at the $60^{th}$ Annual Meeting of the International Water Conference held on Oct. 18–20, 1999.

New methods and techniques for control of cooling water systems are always desirable.

SUMMARY OF THE INVENTION

The instant claimed invention is an autocycle method to control a cooling water system comprising the steps of:
a) adding a treatment product to said cooling water system, with said treatment product comprising inert tracer and tagged treatment polymer in a set proportion;
b) providing a sufficient number of fluorometers,
c) using said sufficient number of fluorometers to measure the fluorescent signal of said inert tracer and the fluorescent signal of said tagged treatment polymer in the water from the cooling water system;
d) using these measured fluorescent signals from step c) to determine the amount of said tagged treatment polymer present in said cooling water system;
e) comparing the amount of said tagged treatment polymer present to the amount of tagged treatment polymer being fed into the system to determine the consumption of said tagged treatment polymer; and
f) using said consumption of said tagged treatment polymer to control the concentration cycles of said cooling water system, with the proviso that said control is implemented by linking any or all of the following parameters
i) the flowrate of the make-up water to the cooling water system;
ii) the flowrate of the treatment product comprising inert tracer and tagged treatment polymer,
iii) frequency and amount of blowdown flowrate from the cooling water system;
iv) overall water flowrate through the cooling tower;
v) overall volume of water in the cooling tower; and
vi) composition of makeup water;
to the consumption of said tagged treatment polymer, with the provisos that:
α) the minimum flowrate of treatment product comprising tagged treatment polymer must be sufficient to supply the cooling water system with the requisite amount of tagged treatment product; and
β) when control is implemented by linking flowrates, the flowrates are balanced.

DETAILED DESCRIPTION OF THE PRESENTLY PREFERRED EMBODIMENTS

For purposes of this patent application, the following terms have the indicated definitions:

"autocycle" refers to a method for automatically controlling the cycles of concentration in a cooling water system based on consumption of a tagged treatment polymer;

"concentration cycles" refer to the amount of a species in the tower water relative to the amount of a species in the make-up water;

"concentration cycle split" is defined as the difference between theoretical cycles of a cooling tower with respect to a specie present in the make-up water which could be consumed by some process (precipitation), usually determined by measuring the concentration of a specie which does not precipitate, and the actual cycles of the specie present in the make-up water which may be consumed. In practice, this can be done by comparing calcium (precipitating ion) cycles with magnesium (less likely to precipitate ion) cycles. The "concentration cycle split" thus gives an indication of the relative measure of scaling in the cooling water system.

"consumption" in general refers to the difference between the amount of tagged treatment polymer fed and the amount of tagged treatment polymer remaining;

"inert" refers to the fact that an inert fluorescent tracer is not appreciably or significantly affected by any other chemistry in the cooling water system, or by the other system parameters such as metallurgical composition, microbiological activity, biocide concentration, heat changes or overall heat content. To quantify what is meant by "not appreciably or significantly affected", this statement means that an inert fluorescent compound has no more than a 10% change in its fluorescent signal, under conditions normally encountered in cooling water systems. Conditions normally encountered in cooling water systems are known to people of ordinary skill in the art of industrial water systems.

"PCT" refers to a Pilot Cooling Tower;

"treatment active" is defined as any component of a treatment chemical that performs a desired function upon addition to a cooling water system.

"tagged treatment polymer" is a polymer that has been "tagged" with a fluorescent moiety wherein said polymer is capable of functioning as a scale or corrosion inhibitor in a cooling water system.

Figure 1:
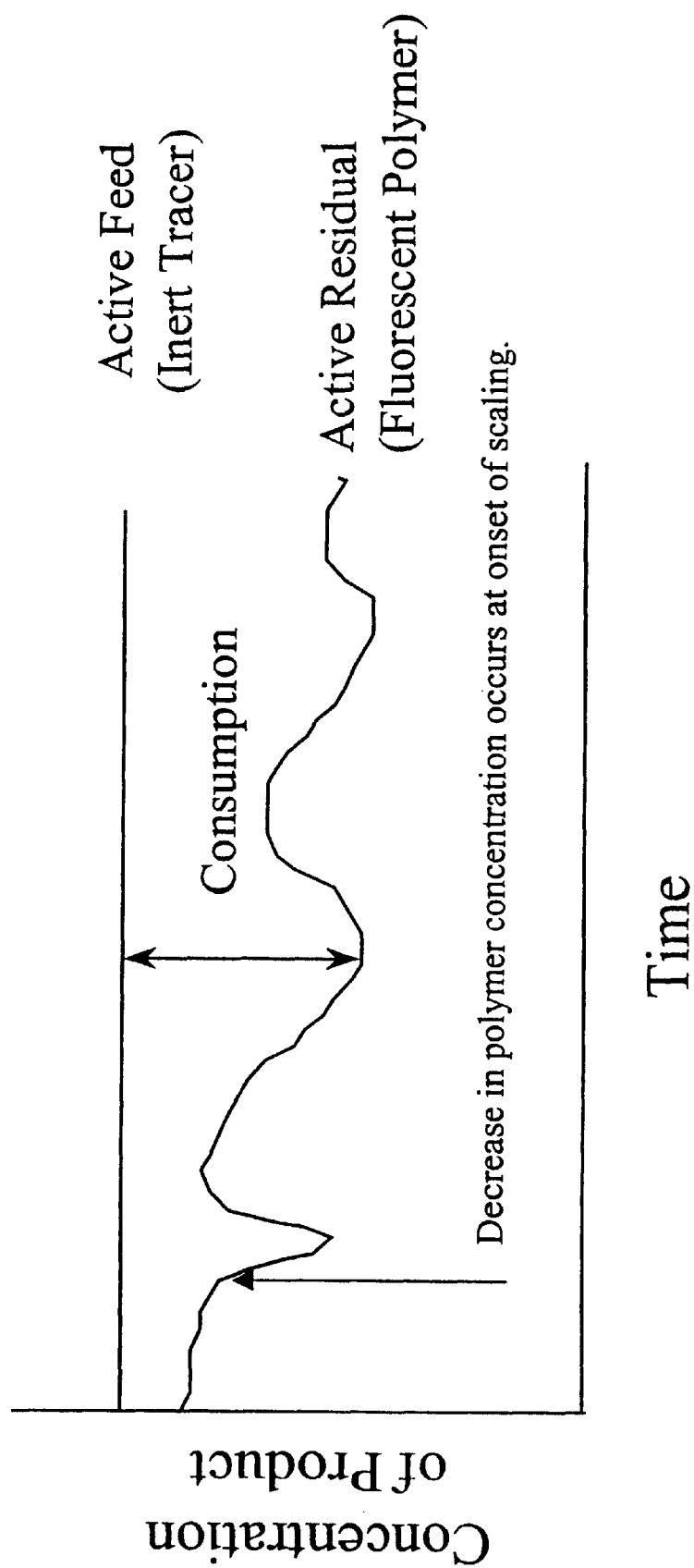
FIG. 1: Conceptual Diagram of Control using Fluorescent Polymer Consumption.

FIG. 1 is a Conceptual Diagram of Control using Fluorescent Polymer Consumption. The data in this diagram was obtained by measuring the fluorescent signal of an inert tracer product and the fluorescent signal of a tagged treatment polymer. The difference between the two signals is indicative of the amount of consumption of the tagged treatment polymer. It has been found that the amount of consumption of a tagged treatment polymer can be used to control the concentration cycles of a cooling water system.

The tagged treatment polymer used in the instant claimed method is selected from the group consisting of polymers described and claimed in U.S. Pat. Nos. 5,128,419; 5,171,450; 5,216,086; 5,260,386 and 5,986,030, U.S. patent application Ser. No. 09/396,681 entitled, FLUORESCENT WATER-SOLUBLE POLYMERS, filed Aug. 31, 1999, now pending, U.S. patent application Ser. No. 09/465,146 entitled, "FLUORESCENT MONOMERS AND POLYMERS CONTAINING SAME FOR USE IN INDUSTRIAL WATER SYSTEMS" filed Dec. 16, 1999, now pending; and U.S. patent application Ser. No. 09,560,881 entitled, FLUORESCENT MONOMERS AND TAGGED TREATMENT POLYMERS CONTAINING SAME FOR USE IN INDUSTRIAL WATER SYSTEMS, filed Apr. 27, 2000, now pending. All patents and patent applications described in this paragraph are herein incorporated by reference.

Preferred tagged treatment polymers are selected from the group consisting of:

59.95 mole % acrylic acid/19.95 mole % acrylamide/20 mole % N-(sulfomethyl)acrylamide/0.1 mole % 8-(4-vinylbenzyloxy)-1,3,6-pyrenetrisulfonic acid, trisodium salt;

59.95 mole % acrylic acid/19.95 mole % acrylamide/20 mole % N-(sulfomethyl)acrylamide/0.1 mole % 8-(3-vinylbenzyloxy)-1,3,6-pyrenetrisulfonic acid, trisodium salt;

59.9 mole % acrylic acid/19.9 mole % acrylamide/20 mole % N-(sulfomethyl)acrylamide/0.2 mole % 4-methoxy-N-(3-N',N'-dimethylaminopropyl)naphthalimide vinylbenzyl chloride quaternary salt; and 59.96 mole % acrylic acid/19.96 mole % acrylamide/20 mole % N-(sulfomethyl)acrylamide/0.08 mole % 4-methoxy-N-(3-N',N'-dimethylaminopropyl) naphthalimide 2-hydroxy-3-allyloxy propyl quaternary salt.

Figure 2:
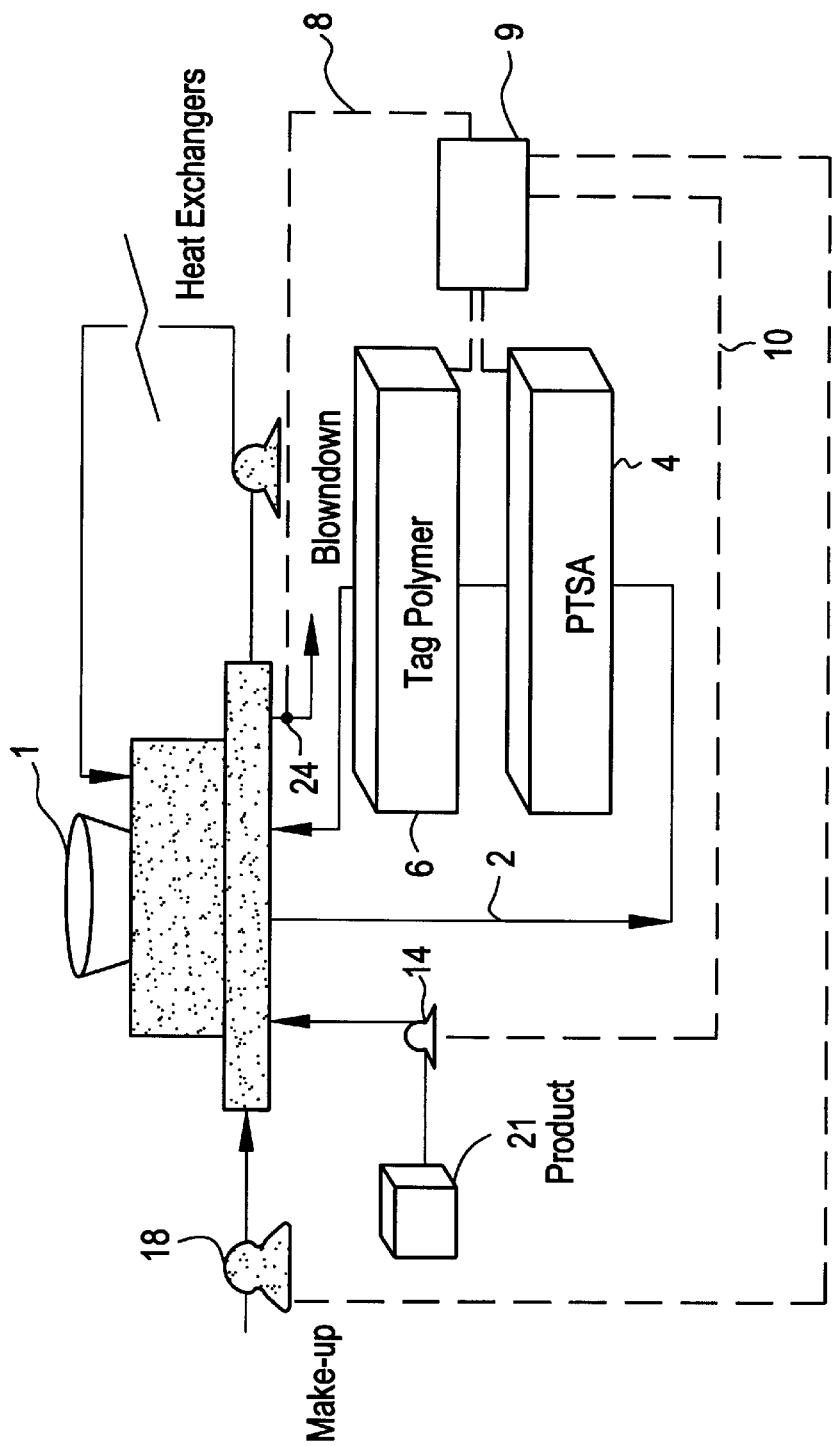
FIG. 2: Schematic of Cooling Water System Control Using Consumption of Fluorescent Tagged Polymer.

A PCT is operated to demonstrate the ability to control concentration cycles in a cooling water system based on consumption of a tagged treatment polymer. Control of this tower is afforded by the scheme shown in FIG. 2. In FIG. 2, cooling tower 1 is directly controlled by the consumption of tagged treatment polymer. Tagged treatment polymer is part of treatment product 21. It is understood that the treatment product contains tagged treatment polymer as well as other ingredients and that treatment product is not equivalent to tagged treatment polymer. Treatment product 21 is pumped to cooling tower 1 through product feed pump 14. Make-up water is added to cooling tower 1 through make-up pump 18. Blowdown from cooling tower 1 is controlled by blowdown pump 24.

In this control scheme, sampling stream 2 flows through two fluorometers. First fluorometer 4 measures the fluorescent signal of the inert fluorescent tracer. Inert fluorescent tracers suitable for use in the instant claimed method are known to people of ordinary skill in the art. One such suitable inert fluorescent tracer is PTSA, which is 1,3,6,8-pyrene tetrasulfonic acid tetrasodium salt. Second fluorometer 6 measures the fluorescent signal of the tagged treatment polymer, which is selected from the group of tagged treatment polymers previously described. These fluorescent signals are sent to controller 9 which is in communication with and can control blowdown pump 24 through signal line 8, product feed pump 14 through signal line 10 and make-up pump 18 through signal line 12. In conducting the method of the instant claimed invention it is not required that controller 9 controls both blowdown pump 24 and make-up pump 18; only one of these pumps need be controlled. For purposes of the description of cooling tower in FIG. 2, signal line 12 to make-up pump 18 is not used.

A suitable fluorometer and controller for use in conducting the method of the instant claimed invention is described and claimed in U.S. patent application Ser. No. 09/563,086 entitled, "MODULAR FLUOROMETER AND METHOD OF USING SAME TO DETECT ONE OR MORE FLUOROPHORES", filed May 1, 2000, now pending, which is herein incorporated by reference in its entirety.

As per standard technology, the feed rate of the treatment product 21 using pump 14 is controlled by the fluorescent signal (converted to the concentration) of the inert fluorescent tracer.

In one possible control scheme, blowdown pump 16 is activated when the % consumption of tagged treatment polymer consumption drops below the level set according to the following equation:

$$\% \text{ Consumption}=(A-B)/A$$

where

A is the amount of treatment product fed to the cooling water system as measured by the inert tracer fluorescent signal, and B is the amount of tagged treatment polymer in the water of the cooling water system as measured by the fluorescent signal of the tagged treatment polymer.

In conducting the method of the instant claimed invention it was found that the amount of treatment product comprising tagged treatment polymer being fed must be sufficient to supply the cooling water system with the requisite amount of tagged treatment polymer required for optimum running of the cooling water system. The amount of tagged treatment polymer required for optimum running of the cooling water system is known to persons of ordinary skill in the art of cooling water systems. The control of feedrate of treatment product can be accomplished by relating the measured consumption of tagged treatment polymer directly to the feedrate of treatment product (using the fluorescent signals of the tagged treatment polymer and inert tracer present in the treatment product to calculate consumption).

In conducting the method of the instant claimed invention it was also found that when control is implemented by linking flowrates, the flowrates must be balanced. For example, if autocycle control is accomplished by linking the flowrate of the treatment product comprising inert tracer and tagged treatment polymer with the flowrate of blowdown, the pump rate of treatment product feed has to be balanced with the blowdown pump rate. If these pump rates are not balanced the result is operation of the cooling tower at two extremes of maximum cycles and minimum cycles. This is undesirable.

If equipment other than pumps is used to control flowrate, this equipment must be operated such that the flowrates are balanced.

One method of achieving a balance in pump rates would be to use pumps with PID (PID stands for "Proportional Integral Derivative") control. Another method of balancing pump rates is to use computer algorithms and software to configure the pumps such that they act like a PID-controlled pump. Two different algorithms have been developed and used to control cooling water systems based on the consumption of a tagged treatment polymer. Both algorithms control a treatment product pump duty cycle over a user defined finite control interval. In both algorithms analog data is obtained at a frequency significantly higher than the control interval. Also in both algorithms, the maximum pump duty cycle will be less than or equal to the control interval such that at each control interval, the pump state should be off.

The first control algorithm is based on increasing the pump duty cycle by some increment or resetting it to a base value at each control interval as consumption conditions warrant. In this algorithm, two analog input signals A and B are monitored at a user defined interval. As previously stated, A is the amount of treatment product fed to the cooling water system as measured by the inert tracer fluorescent signal, and B is the amount of tagged treatment polymer in the water of the cooling water system as measured by the fluorescent signal of the tagged treatment polymer.

One relay (Relay Zero), used to provide power to the product feed pump, is controlled at each interval directly by the response from channel A. If A exceeds a user defined upper setpoint, Relay Zero is toggled off. If A is less than a user defined lower setpoint, Relay Zero is toggled on. Otherwise, Relay Zero status is unchanged.

An arithmetic operation (Op) is applied to channels A and B to determine consumption of the active component. Arithmetic operations may be A–B (Consumption), (A–B)/A (% Consumption), or B/A (the ratio of tagged treatment polymer remaining in the system relative to the tagged treatment polymer fed to the system). Values of Op are stored over a user-defined number of intervals, and a least squares linear regression analysis is applied to that data as a function of time at each interval. The regression analysis returns the slope, dOp/dt.

A second relay (Relay One) is controlled based on values of dOp/dt, as described below. In most cases Relay One primary purpose is to power the blowdown pump or valve solenoid. However, Relay One could also be used to energize an acid feed pump or to energize a make-up water pump or valve solenoid.

The data is examined at the user defined finite control interval. If A is less than its lower setpoint, no further processing takes place until the next control interval and Relay One remains Off.

If Op is less than a user defined operational setpoint or dOp/dt is≦(less than or equal to) 0, the pump duty cycle for Relay One is set to 0 and no further processing takes place till the next control interval.

If A is greater than its lower setpoint, and Op is greater than a user defined operational setpoint, and dOp/dt is greater than 0, the pump duty cycle for Relay One is incremented and Relay One is energized for that duration.

The second control algorithm is based on setting the pump duty cycle for Relay One proportionally based on the Op response. Relay Zero is again used to provide power to a product feed pump, while Relay One is used to energize a blowdown pump or valve solenoid.

As with algorithm 1, two analog input signals A and B, as previously defined, are monitored at a user defined interval. Relay Zero is controlled at each interval directly by the response from channel A. If A exceeds a user defined upper setpoint, Relay Zero is toggled off. If A is less than a user defined lower setpoint, Relay Zero is toggled on. Otherwise, Relay Zero status is unchanged.

The data is also examined at a user defined finite control interval. If A is less than its lower setpoint, no further processing takes place until the next control interval.

If A is greater than its lower setpoint, a proportional response (K) between two user defined operational setpoints is determined for the arithmetic operation (Op) applied to channels A and B. Arithmetic operations are the same as given above (i.e. A–B, (A–B)/A, or B/A). If Op exceeds the upper operational setpoint, K is set to 1. If Op is less than the lower operational setpoint, K is set to 0.

At each interval, Relay One is energized for a period of time equivalent to a user defined maximum interval times K. The user defined maximum interval should not exceed the decision interval.

One of the major advantages of % polymer consumption control, as compared to conductivity control, is that control is possible to maintain even if the composition of the make-up water changed. In some parts of the world, the composition of make-up water is quite variable and having the ability to control even when the make-up water changes is a huge advantage over the currently available conductivity control method.

The following example is intended to be illustrative of the present invention and to teach one of ordinary skill in the art how to make and use the invention. These examples are not intended to limit the invention in any way.

EXAMPLES

Example 1

A PCT configured the same as shown in FIG. 2 was controlled at a treatment product feed rate of 250 ppm and 15% tagged polymer consumption. The controller was set to control the treatment product pump (pump 14, Relay Zero) and the blowdown pump (pump 24, Relay One). The water used in the PCT did not have measurable background fluorescence.

Figure 3:
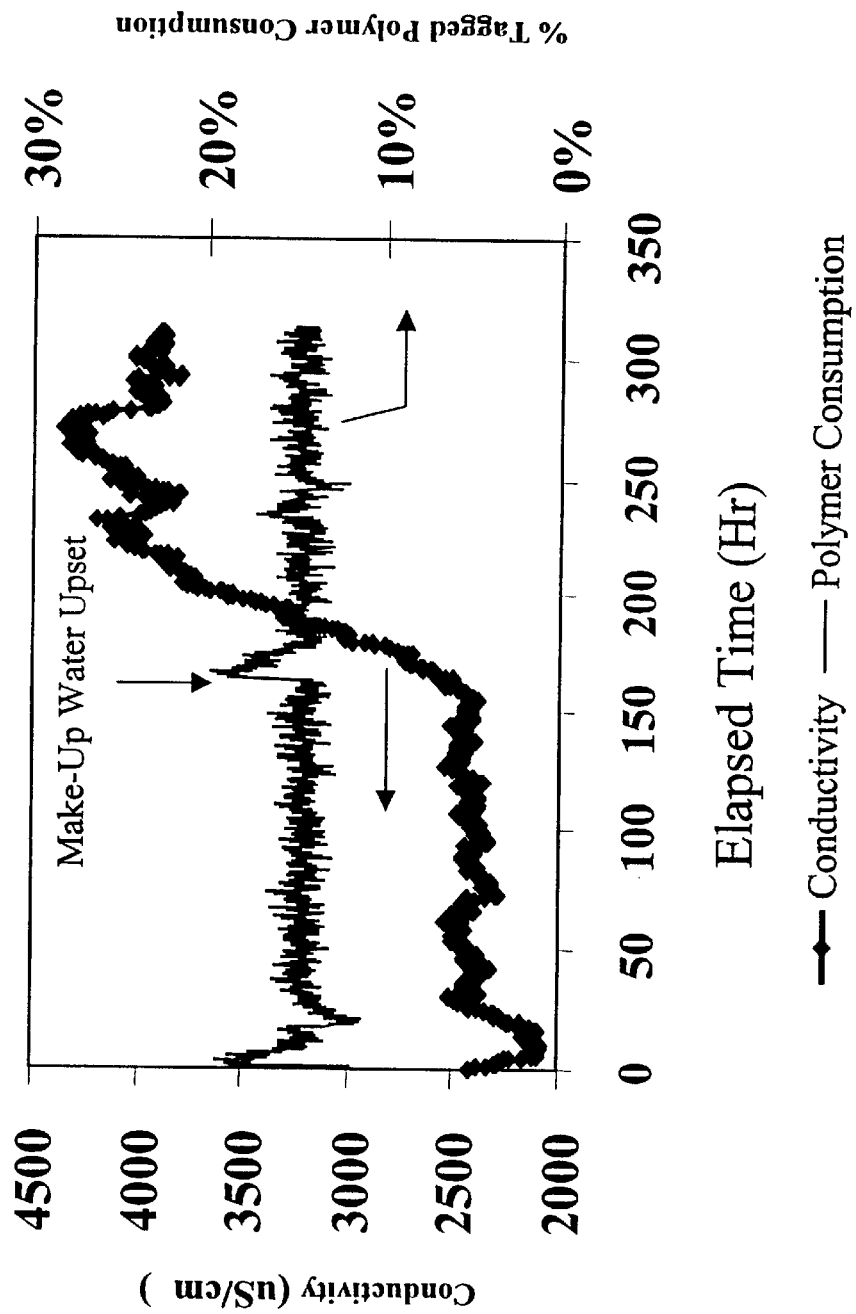
FIG. 3: Control of Pilot Cooling Tower Using Consumption Control During Make-Up Water Upset.

FIG. 3 shows the % polymer consumption and conductivity during a make-up water upset. At 150 hours of elapsed time ("ET"), the make-up water source was changed. The first make-up water source contained 150 ppm Ca (as $CaCO_3$), 75 ppm Mg (as $CaCO_3$), 110 ppm total alkalinity (as $CaCO_3$), and 72 ppm sulfate (as $SO_4$), with a conductivity of approximately 670 $\mu$S/cm. The second make-up water source contained 300 ppm Ca (as $CaCO_3$), 150 ppm Mg (as $CaCO_3$), 110 ppm total alkalinity (as $CaCO_3$), and 249 ppm sulfate (as $SO_4$), with a conductivity of approximately 1190 $\mu$S/cm. The second make-up water source contained higher levels of hardness and sulfate, as indicated by the higher conductivity. However, the tendency of the second make-up water to form scale (predominantly $CaCO_3$), was actually less than the first make-up water source, because of the increased levels of sulfate. (Under the conditions of this test, calcium sulfate is soluble and does not form a calcium sulfate precipitate.) The controller maintained the polymer consumption level, and allowed the tower to cycle to higher cycles of concentration as indicated by the increase in conductivity. The concentration cycles splits (after adjustment for the differences in hardness) were the same for both make-up water sources; this indicates that control of the cooling water system, with respect to scale was also maintained.

For comparison, a similar make-up water upset was done with a tower configured such that treatment product feed rate was controlled at 250 ppm, but blowdown was controlled by conductivity. This is a known method to control cooling water systems. Since control of this tower was maintained by conductivity, the amount of blowdown was much higher than was needed to maintain control of the tower, with respect to scale. During this upset, since conductivity was controlled, the % polymer consumption dropped because the second make-up water had a decreased tendency to form scale.

A comparison of the blowdown rates, makeup rates and treatment product required during the make-up water upset under consumption control and under conductivity control (comparative example) are given in Table 1.

TABLE 1

Comparison of Cooling Tower Operation under Consumption and Conductivity Control during a Make-Up Water Upset

| Control Method | Blowdown Rate (gal/day) | Make-Up Water Rate (gal/day) | Relative Treatment Product Usage |
|---|---|---|---|
| Consumption (Example) | 10.2 | 34.7 | 1 |
| Conductivity (Comparative Example) | 24.5 | 49.0 | 2.4 |

Operation of the cooling tower is maintained in both examples, but the amount of blowdown, make-up and treatment product is much less under consumption control, compared to conductivity control. Therefore, autocycle consumption based control means maintaining control of scale with less blowdown and less blowdown means savings for the operator of the cooling water system, in terms of water costs and treatment product costs. This means that consumption control results in much more efficient operation without any adverse effect on operating performance.

It should be understood that various changes and modifications to the presently preferred embodiments described herein would be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. An autocycle method to control a cooling water system comprising the steps of:

a) adding a treatment product to said cooling water system, with said treatment product comprising inert tracer and tagged treatment polymer in a set proportion;

b) providing a sufficient number of fluorometers, c) using said sufficient number of fluorometers to measure the fluorescent signal of said inert tracer and the fluorescent signal of said tagged treatment polymer in the water from the cooling water system;

d) using these measured fluorescent signals from step c) to determine the amount of said tagged treatment polymer present in said cooling water system;

e) comparing the amount of said tagged treatment polymer present to the amount of tagged treatment polymer being fed into the system to determine the consumption of said tagged treatment polymer; and f) using said consumption of said tagged treatment polymer to control the concentration cycles of said cooling water system, with the proviso that said control is implemented by linking any or all of the following parameters i) the flowrate of the make-up water to the cooling water system;

ii) the flowrate of the treatment product comprising inert tracer and tagged treatment polymer;

iii) frequency and amount of blowdown flowrate from the cooling water system;

iv) overall water flowrate through the cooling tower;

v) overall volume of water in the cooling tower; and vi) composition of makeup water;

to the consumption of said tagged treatment polymer, with the provisos that:

α) the minimum flowrate of treatment product comprising inert tracer and tagged treatment polymer must be sufficient to supply the cooling water system with the requisite amount of tagged treatment product; and β) when control is implemented by linking flowrates, the flowrates are balanced.

* * * * *